United States Patent [19]

Wheeler

[11] Patent Number: 4,492,799
[45] Date of Patent: Jan. 8, 1985

[54] HALO-4-ALKENOIC ACIDS AND THEIR USE AS PESTICIDAL INTERMEDIATES

[75] Inventor: Thomas N. Wheeler, Charleston, W. Va.

[73] Assignee: Union Carbide Corporation, Danbury, Conn.

[21] Appl. No.: 54,209

[22] Filed: Jul. 2, 1979

[51] Int. Cl.³ .................. C07C 61/40; C07C 59/40
[52] U.S. Cl. .................................... 562/506; 562/598; 562/574; 562/504; 562/505; 562/588; 562/586; 562/472; 562/431; 562/514; 562/429; 260/465.4
[58] Field of Search .............. 562/598, 507, 505, 506, 562/504, 474, 472, 588, 471, 431, 429, 552; 560/219; 260/465.5

[56] References Cited

U.S. PATENT DOCUMENTS

| 3,338,960 | 8/1967 | Mador | 562/598 |
| 3,872,141 | 3/1975 | Weis et al. | 562/588 |
| 4,042,710 | 8/1977 | Bull et al. | 424/304 |
| 4,058,622 | 11/1977 | Fujimoto et al. | 260/465.4 |
| 4,161,536 | 7/1979 | Drabek et al. | 562/598 |

FOREIGN PATENT DOCUMENTS 862499  6/1978  Belgium ............................ 562/588

OTHER PUBLICATIONS

Gyulikeukhym et al., Chem. Abst. vol. 80, #81951d (1974).
Saakyan et al., Chem. Abst., vol. 70, #3222e (1969).

Primary Examiner—James H. Reamer
Attorney, Agent, or Firm—C. J. Vicari

[57] ABSTRACT

Novel halo-4-alkenoic acid compounds which are useful intermediates for the synthesis of insecticides and miticides.

5 Claims, No Drawings

HALO-4-ALKENOIC ACIDS AND THEIR USE AS PESTICIDAL INTERMEDIATES

BACKGROUND OF THE INVENTION

1. Field of the Invention

This invention relates to novel halo-4-alkenoic acids and to their prepationon. More particularly, this invention relates to novel halo-4-alkenoic acids which are useful intermediates for the synthesis of insecticides and miticides and methods of their preparation.

2. Description of the Prior Art

Certain related halo-4-alkenoic acids reported in the literature are summarized in Table I below:

TABLE I

Known Halo-4-Alkenoic Acids having the following structural formula I:

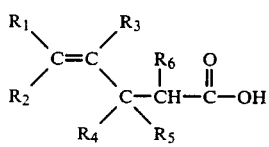

| $R_1$ | $R_2$ | $R_3$ | $R_4$ | $R_5$ | $R_6$ | Chem. Abstracts Reference |
|---|---|---|---|---|---|---|
| H | H | Br | H | H | $-CH_2CH_3$ | 55:11293d |
| H | H | Br | H | H | $-n-C_3H_7$ | 55:11293d |
| H | H | Br | H | H | $-i-C_3H_7$ | 55:11293d |
| H | H | Br | H | H | $-n-C_4H_9$ | 54:1286b |
| H | H | Br | H | H | $-i-C_4H_9$ | 55:11293d |
| H | H | Cl | H | H | $-CH_3$ | 55:20946f |
| H | H | Cl | H | H | $-CH_2CH_3$ | 55:20946f |
| H | H | Cl | H | H | $-n-C_3H_7$ | 55:20946f |
| H | H | Cl | H | H | $-i-C_5H_{11}$ | 55:20946f |
| Cl | H | H | H | H | $-CH_3$ | 55:20951a |
| Cl | H | H | H | H | $-CH_2CH_3$ | 55:20951a |
| Cl | H | H | H | H | $-n-C_3H_7$ | 55:20951b |
| Cl | H | H | H | H | $-n-C_4H_9$ | 55:20951a |
| Cl | H | H | H | H | $-i-C_4H_9$ | 55:20951b |
| Cl | H | H | H | H | $-i-C_5H_{11}$ | 55:20951b |
| Cl | Cl | H | H | H | $-CH_2CH_3$ | 70:3222c |
| Cl | Cl | H | H | H | $-n-C_3H_7$ | 66:54994h |
| Cl | Cl | H | H | H | $-n-C_4H_9$ | 70:3222e |
| Cl | Cl | H | H | H | $-i-C_5H_{11}$ | 70:3222e |
| $CH_3$ | Cl | H | H | H | $-CH_3$ | 80:81951n; 53:21649c |
| $CH_3$ | Cl | H | H | H | $-CH_2CH_3$ | 80:81951n |
| $CH_3$ | Cl | H | H | H | $-n-C_3H_7$ | 80:81951n; 54:283i |
| $CH_3$ | Cl | H | H | H | $-i-C_3H_7$ | 54:1400g |
| $CH_3$ | Cl | H | H | H | $-n-C_4H_9$ | 40:3397 |
| $CH_3$ | Cl | H | H | H | $-i-C_4H_9$ | 80:81951n |
| $CH_3$ | Cl | $CH_3$ | H | H | $-CH_2CH_3$ | 71:70046j |
| $CH_3$ | Cl | $CH_3$ | H | H | $-i-C_4H_9$ | 71:70046j |
| $CH_3$ | Cl | $CH_3$ | H | H | $-i-C_5H_{11}$ | 71:70046j |
| $CH_3$ | Cl | $CH_3$ | H | H | $-n-C_5H_{11}$ | 71:70046j |
| $CH_3$ | Cl | $CH_3$ | H | H | $-n-C_3H_7$ | 71:70046j |

All of the acids shown in Table I above were prepared by the malonic ester synthesis, a typical example of which is shown below (as described in M. T. Dangyan and G. M. Shakhnazaryan, Zvest., Akad. Nauk Armyan, S.S.R. Khim. Nauki 13, No. 4, 259–62 (1960)).

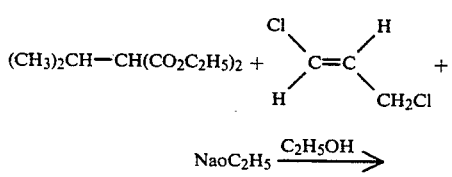

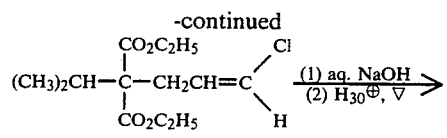

32% yield

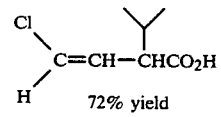

72% yield

Belgium Pat. No. 860,687 discloses phenoxybenzyl haloalkenoate esters which are useful as insecticides and acaricides and have the following structural formula II:

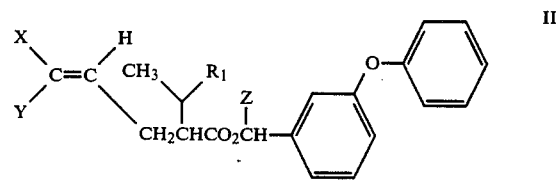

wherein: X is halogen, Y is halogen or $CH_3$, Z is CN or ethynyl, and $R_1$ is H or $CH_3$. The esters of Belgium Pat. No. 860,687 are prepared using acids exemplified by the structural formula:

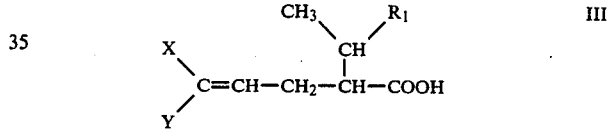

wherein X, Y and $R_1$ are as defined in formula II hereinabove.

Belgium Pat. No. 862,499 discloses a group of pyrethroidal esters which are characterized by the so-called "pydrinalcohol" and a class of olefinic esters. The pesticidal phenoxy benzyl pentene carboxylates are prepared by esterifying a phenoxy benzyl alcohol with pentene carboxylic acid. According to the disclosure of Belgium Pat. No. 862,499, the pyrethroid esters are prepared using a synthetic method from acids of the general formula IV:

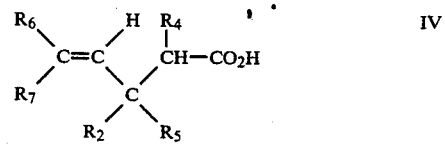

wherein
$R_4$ = lower alkyl having from 1 to 4 carbon atoms
$R_2$ and $R_5$ = H or lower alkyl
$R_6$ and $R_7$ = Cl or Br

BRIEF SUMMARY OF THE INVENTION

This invention describes the composition and synthesis of a series of novel halo-4-alkenoic acids generalized by the following structure V:

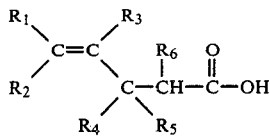

wherein:

$R_1$, $R_2$, and $R_3$ are independently H, a lower alkyl group having from 1 to 3 carbon atoms or halogen;

$R_4$ and $R_5$ are independently H, a lower alkyl group having from 1 to 3 carbon atoms, polyhaloalkyl, haloalkyl, halogen, a lower alkenyl group having from 2 to 3 carbon atoms, a lower cycloalkyl group having from 3 to 5 carbon atoms, a lower cycloalkenyl group having from 3 to 5 carbon atoms, cyano, nitro, a lower alkoxy group having from 1 to 3 carbon atoms, arloxy, a lower alkylthio group having from 1 to 3 carbon atoms, arylthio, a lower alkylsulfinyl group having from 1 to 3 carbon atoms, arylsulfinyl, a lower alkylsulfonyl group having from 1 to 3 carbon atoms, arylsulfonyl, acylamido, or a lower dialkylamino group having from 1 to 3 carbon atoms;

$R_6$ is selected from the group consisting of: (1) cycloalkyl, alkenyl, branched alkenyl, or cycloalkenyl; or (2) a branched alkyl group having from 3 to 5 carbon atoms or an alkyl group having from 1 to 5 carbon atoms, with the proviso that $R_4$ or $R_5$ is other than hydrogen.

Structure V is understood to include geometrical isomers about the $C_4$–$C_5$ bond and optical isomers at $C_2$.

These acid compounds generalized by structure V, with varying degrees of efficiency, are useful intermediates for the synthesis of insecticides and miticides. In general, the acid compounds which can be used to synthesize compositions having the greatest degree of pesticidal activity are those in which only one of $R_4$ or $R_5$ is methyl. The preferred acid compounds of this invention are those in which $R_1$ and $R_2$ are halogen preferably chlorine; wherein only one of $R_4$ or $R_5$ is methyl; and wherein $R_6$ is isopropyl or cyclopropyl.

When esterified with appropriate alcohols (using any of several conventional esterification techniques), the novel acids of this invention yield esters which exhibit broad-spectrum insecticidal and miticidal activity. These esters also have the advantages of relatively low toxicity to mammals and little or no phytotoxicity.

Halo-4-alkenoic acid compounds of this invention may by synthesized by a variety of methods. These methods are summarized below:

Synthesis

A variety of methods may be used to synthesize the novel halo-4-alkenoic acids. These methods are summarized below.

Method 1

(1) 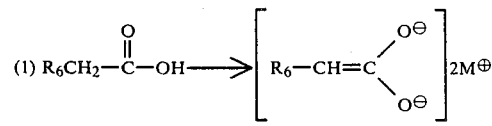

(2) 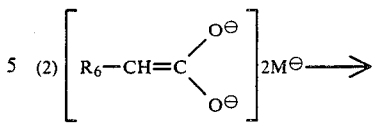

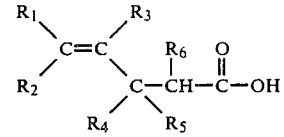

Method 2

(1) 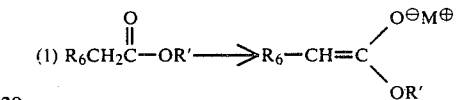

(2) 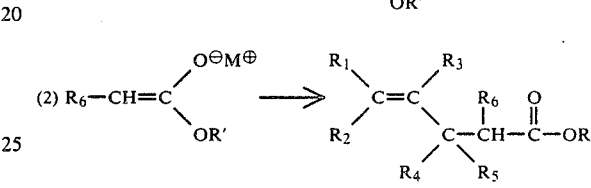

(3) 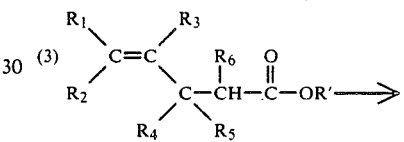

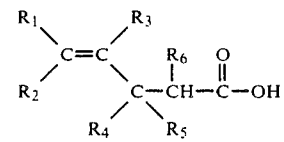

Method 3

(1) 

(2) 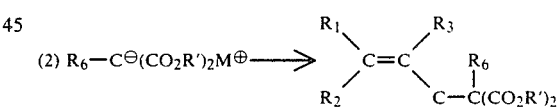

(3) 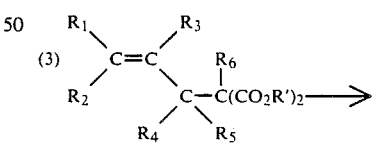

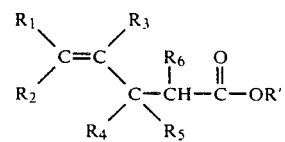

(4) 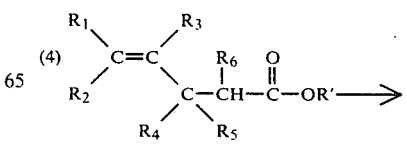

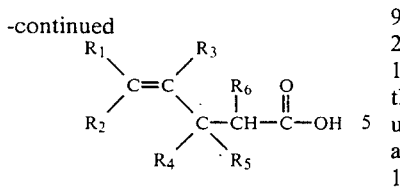

Method 4

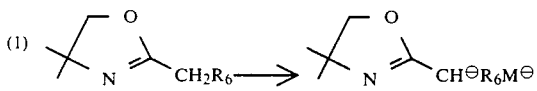

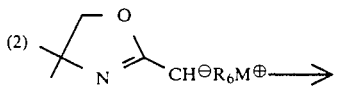

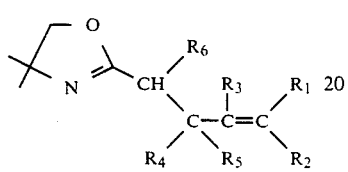

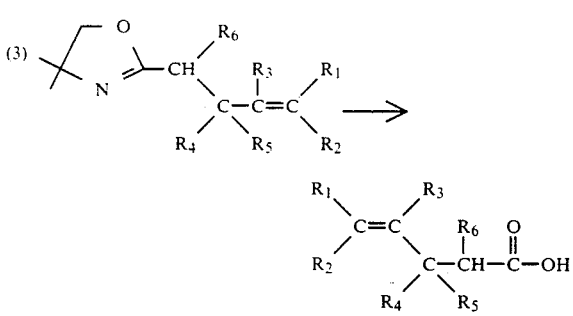

Method 5

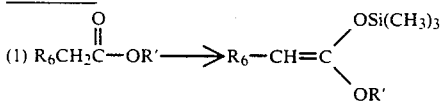

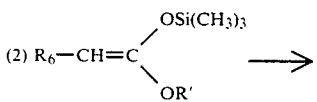

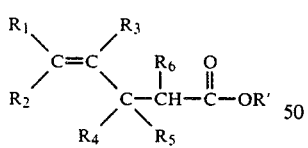

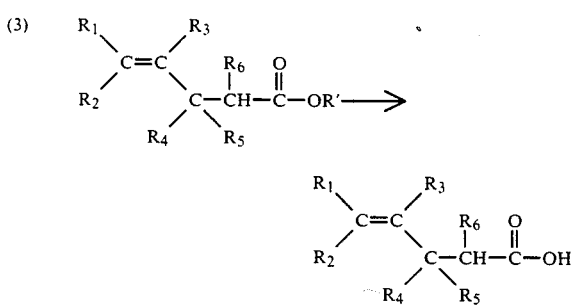

Methods 1 and 2 have been well documented in the chemical literature as useful for preparing alkylsubstituted acetic acids (see P. L. Creger, *J. Amer. Chem. Soc.*, 92, 1397 (1970); M. W. Rathke, A. Lindert, Ibid., 93, 2318 (1971); R. J. Cregge et al., *Tet. Letters*, 1973, 2425; J. A. MacPhee et al., *J. Chem. Soc. Perkin I*, 694, 1977). These two methods differ only in the nature of the starting material, i.e. in method 1 an acid enolate is used and in method 2 an ester enolate is employed. The alkali metal salts of the acids may also be used in method 1. In both methods 1 and 2, a strong base is required to form the required enolate. Suitable bases for effecting step (1) of methods 1 and 2 are the lithium amides formed from a variety of secondary amines. These lithium amides are sufficiently strong bases to form the required enolates and the lithium cation chelates the enolates thereby improving their stability and solubility in organic solvents. Examples of suitable bases which may be used are lithium diethylamide, lithium diisopropylamide (LDA), lithium isopropylcyclohexylamide, lithium bis(trimethylsilyl) amide, and the like.

In step 2 of methods 1 and 2 an allylic halide is used to alkylate the enolate anion. Side reactions involving an elimination pathway are possible in this step. If the halide contains alkyl substituents at $R_4$ and $R_5$, elimination to form a 1,3-butadiene is a competing side reaction. A second elimination pathway is dehydrohalogenation of the halo-4-alkenoic acids. These side reactions can be reduced by adding the allylic halide to the lithium enolates at low temperatures and by the use of relatively non-polar solvents.

Suitable solvents for methods 1 and 2 include 1,2-dimethoxyethane, ethyl ether, tetrahydrofuran, benzene, toluene, hexane, and other similar organic solvents which do not react with the reagents employed.

The reactions illustrated by the general scheme given in methods 1 and 2 may be conducted over the range of $-100°$ C. to $+50°$ C. Preferably, these reactions are run at $-76°$ C. to $0°$ C. and at autogenous pressure.

Method 3 is a versatile route for the preparation of the acids of this invention.

Method 4 has been reported in the literature as a versatile technique for synthesizing homologated acetic acids (see A. I. Meyers et al., *J. Org. Chem.*, 39, 2778 (1974)). The required 2-alkyl-4,4-dimethyl-2-oxazolines required in step (1) of method 4 can be readily prepared by treating 2-amino-2-methyl-1-propanol with the appropriate alkylacetic acid and removal of the 2-oxazoline by distillation (see P. Allen and J. Ginos, *J. Org. Chem.*, 28, 2759 (1963)).

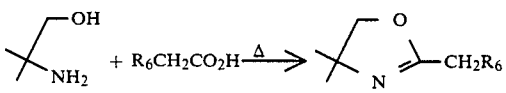

In step (2) of method 4, the lithium salt of the 2-alkyl-4,4-dimethyl-2-oxazoline was prepared using an organolithium reagent (n-butyl-lithium, methyl lithium, etc.) as the base. The same solvents described above for step (1) of methods 1 and 2 may be utilized in this step. The lithium salt of the 2-oxazoline is preferably formed and used at low temperatures, e.g. $-76°$ C. to $0°$ C. The second step in method 4, alkylation of the lithium salt of the 2-oxazoline is carried out under conditions identical to those described above for this step in methods 1 and 2

The final step in method 4, hydrolysis of the 2-alkyl-4,4-dimethyl-2-oxazoline, is readily affected by refluxing in aqueous mineral acid. The desired carboxlic acids are obtained in high yields.

Method 5 has been reported in the literature as a route to α-tert-butylacetic acid esters (see M. T. Reetz and K. Schwellnus, *Tet. Let.*, 1455, 1978). Step (1) method 5 involves the synthesis of alkyltrimethylsilyl acetals of ketenes (see C. Ainesworth et al., *J. Organomet. Chem.*, 46, 59 (1972)). These ketene intermediates are synthesized by treatment of the readily available alkyl acetates with lithium amide bases to form the enolate which is then trapped by reaction with chlorotrimethylsilane. The reaction conditions, solvents, and reagents for this step are identical to those described for step (1) of methods 1 and 2 above. The ketene alkyltrimethylsilyl acetals isolated in step (1) of method 5 may be distilled, but they must not be allowed to come in contact with acid or moisture.

In step (2) of method 5 the ketene alkyltrimethylsilyl acetals are alkylated with allylic halides in the presence of a Lewis acid catalyst. A variety of Lewis acids, e.g. boron trifluoride, aluminum chloride, ferric chloride, antimony pentafluoride, stannic chloride, or zinc chloride, may be utilized in this alkylation. The Lewis acid is used in catalytic amounts, preferably in the range of 1-5 mol percent. Any organic solvent that is compatible with the reagents may be used in step 2 of method 5. A preferred solvent/catalyst combination for this step is zinc chloride and methylene chloride. Step (2) of method 5 is not critically dependent on temperature and may be carried out over a range of temperature from $-30°$ C. to $+50°$ C. and at autogenous pressures. The reaction is preferably carried out at room temperature ($30°$ C.).

The following specific examples are presented to more particularly illustrate the manner in which the compounds of this invention may be prepared:

EXAMPLE I 4-chloro-2-isopropyl-4-pentenoic acid

A 1 liter flask was equipped with a mechanical stirrer, reflux condenser, nitrogen inlet, addition funnel, and thermometer. The flask was charged with 200 ml of tetrahydrofuran (THF) and 31.37 g (0.300 mol) of diisopropylamine and cooled to $-4°$ C. The n-butyllithium solution (265 ml of 1.6M, 0.424 mol) was added dropwise at $-4°$ to $-6°$ C. over 22 minutes. The reaction mixture was then stirred for 30 minutes at $-4°$ C. and then 39.06 g (0.300 mol) of ethyl isovalerate added over 15 minutes. The reaction mixture was cooled to $-78°$ C. and 44.39 g (0.400 mol) of 2,3-dichloro-1-propene added dropwise. During the addition of the halide, the temperature was maintained at $-78°$ C. to $-74°$ C. The reaction mixture was stirred for 2 hrs. at $-78°$ C. to give a clear, tan colored solution. The temperature of the reaction mixture was then allowed to rise to $-40°$ C., and stirred at $-40°$ C. to $-30°$ C. for 2 hours. The reaction mixture was then allowed to stand at room temperature over the weekend. The reaction mixture was quenched with 25 ml of water and then poured into 300 ml of ice water. The aqueous mixture was extracted twice with 250 ml portions of ether. The combined ether extracts were washed with saturated sodium chloride solution, dried (MgSO$_4$), and the ether removed. The residue was vacuum distilled through a vigreux column to give 28.02 g (46% yield) of ethyl 4-chloro-2-isopropyl-4-pentenoate, bp 53°-63° C./0.70 mm.

IR(neat, cm$^{-1}$): 2955(s), 2940(m), 2870(m), 1730(s), 1630(m), 1460(2), 1370(w), 1260(w), 1230(2), 1220(w), 1175(s), 1140(m), 1025(m), 890(m).

NMR(CDCl$_3$,δ): 0.95(m,6H); 1.20(t,3H); 1.6-2.8(m,4H), 4.15(q,2H); 5.18(s,2H).

The ethyl 4-chloro-2-isopropyl-4-pentenoate (8.0 g, 0.039 mol) was refluxed for 20 hrs. in 15 ml of water and 15 ml of ethanol containing 4.8 g (0.12 mol) of sodium hydroxide. Most of the ethanol was removed on the rotary evaporator and the residue taken up in 100 ml of water. The aqueous solution was extracted with two 50 ml portions of ether, then acidified with conc. HCl. The acidified mixture was extracted twice with 100 ml of ether. The ether was washed with water, dried (MgSO$_4$), and removed to leave 4.83 g (70% yield) of a light yellow oil.

IR(neat, cm$^{-1}$): 3500-2500 (s,broad), 1700(s), 1638(s), 1460(m), 1430(s), 1390(w), 1370(w), 1280(m), 1240(m), 1220(m), 1250(m), 1140(m), 920(m), 880(s).

NMR(CDCl$_3$,δ): 1.00(d,6H); 1.4-2.9(m,4H); 5.18(s,2H); 11.13(s,1H).

EXAMPLE II

Preparation or 5,5-dichloro-3-methyl-2-cyclopropyl-4-pentenoic acid

Part A: 1,1,1,-trichloro-3-bromobutane

A 3l Adkins stainless steel bomb was thoroughly cleaned, dried and purged with nitrogen. The bomb was charged with 594.8 g (3.0 mol) of bromotrichloromethane 5.00 g (0.02 mol) dibenzoyl peroxide. The bomb was then sealed and cooled in a dry-ice acetone bath for 30 minutes. The bomb was then charged with 69 g (1.62 mol) propylene via a small hoke cylinder. The bomb was then agitated and heated for 4 hours during which time a temperature rise of 44° C. and a pressure increase of 100 PSIG was observed within 15 minutes. The reaction mixture was an almost colorless liquid which was vacuum distilled through a vigreaux column to give 426 g (87% yield) of the desired product b.p. 59°-65° C./10 mm.

NMR (CDCl$_3$,δ): 1.85 (d, 3H); 3.32 (m, 2H); 4.40 (m, 1H).

Part B: 1,1,1-trichloro-2-butene

A 3 liter flask was equipped with a magnetic stirrer, addition funnel, and nitrogen inlet. The flask was charged with 69.19 g (1.05 mol) of 85% potassium hydroxide dissolved in 500 ml of ethanol and the solution cooled in a salt-ice bath. To this solution was added dropwise 316.8 g (1.05 mol) of 1,1,1-trichloro-3-bromobutane in 100 ml of ethanol over a 1 hour period. A white precipitate forms upon the addition of the butane. After the addition was complete the reaction mixture was stirred for 3½ hours at 0° C. The reaction mixture was diluted with 1800 ml of cold water and extracted three times with 300 ml portions of hexane. The combined hexane extracts were washed with water, dried (MgSO$_4$), and concentrated by distillation at atmospheric pressure. The residue was vacuum distilled through a vigreaux column to give 153.15 g (91% yield) of 1,1,1-trichloro-2-butene, b.p. 72°-79° C./100 mm.

NMR (CDCl$_3$,δ): 1.87 (d, 3H); 6.25 (m, 2H).

Part C: 1,1,3-trichloro-1-butene

A 500 ml flask fitted with a magnetic stirrer, reflux condenser and nitrogen inlet was charged with 152.31 g (0.96 mol) of 1, 1, 1-trichloro-2-butene and 6.00 g (0.044 mol) of anhydrous zinc chloride. The reaction mixture was stirred for 16 hrs. at 25° C. The mixture was filtered through celite to 146.09 g (96% yield) of the 1,1,3-trichloro-1-butene as a colorless liquid.

NMR (CDCl$_3$, δ): 1.61 (d, 3H); 4.8 (m, 1H); 6.05 (d, 1H)

Part D: cyclopropaneacetonitrile

A 1 liter flask was fitted with a mechanical stirrer, thermometer reflux condenser, addition funnel, and a nitrogen inlet. The flask was charged with 61.06 g (1.25 mol) of sodium cyanide and 471 ml of dimethyl sulfoxide and warmed to 70° C. Added dropwise was 100.0 g (1.10 mol) of chloromethyl cyclopropane at a rate to sustain the temperature at 70°–75° C. When the addition was complete the reaction was heated to 75° C. for 2 hours. The mixture was cooled, poured into 2 liters of water and extracted 4 times with 300 ml of ether. The combined ether extracts were washed 2 times with 100 ml of water, dried (MgSO$_4$), and the ether was removed. The residue was distilled through a vigreaux column to 74.82 g (82% yield) of cyclopropaneacetonitrile as a colorless liquid, b.p. 97°–99°/10 mm. NMR (CDCl$_3$δ): 0–1.3 (m, 5H); 2.37 (d, 2H)

Part E: diethyl cyclopropyl malonate

A 2 liter flask was equipped with a mechanical stirrer, reflux condenser, thermometer, Dean-Stark trap, and a nitrogen inlet. The flask was charged with 480 ml of ethanol and 39.8 g (1.29 mol) of sodium and was heated until the sodium dissolved. Most of the ethanol was distilled off and 480 ml of diethyl carbonate added over 10 minutes. The ethanol was distilled off again until the reaction temperature reached 240° C. and 250 ml of additional diethyl carbonate was added. The mixture was cooled to 15° C. and 72.19 g (0.88 mol) of cyclopropanteacetonitrile was added dropwise over a 10 minute period. The reaction mixture was slowly warmed to 100° C. and held there until all foaming subsided and the reaction temperature reached 110° C, where it was held for 30 minutes. The mixture was cooled to room temperature, ice added and extracted with ether. The basic aqueous layer was cooled in ice, acidified with ice cold 6N HCl and extracted 3 times with 250 ml of ether. The combined ether solution was dried (MgSO$_4$) and the ether removed at less than 40° C. under reduced pressure. This residue was dissolved in 535 ml of dry ethanol and charged to a 2 liter flask equipped with a mechanical stirrer, reflux condenser, nitrogen inlet, and gas diffusion tube. The reaction mixture was cooled to 0° C. and anyhydrous HCL was added until saturation was reached at 0° C.; then the reaction mixture was stirred for 1 hour at 0° C., then at room temperature for 30 minutes, then at reflux for 16 hours. The reaction was cooled to room temperature and filtered, the filtrate diluted with 1 liter water and extracted 4 times with 300 ml of ether. The ether extracts were combined and washed with water, dried (MgSO$_4$) and ether removed. The residue was distilled through a vigreaux column to give 97 g (92% yield) of diethyl cyclopropyl malonate as a colorless liquid, b.p. 125°–127° C./21 mm. NMR (CDCl$_3$, δ): 0.1–1.5 (m, 11H); 2.65 (d, 1H); 4.21 (q, 4H).

Part F: diethyl (3,3-dichloro-1-methyl-2-propenyl) cycloproply malonate

A 1 liter flask was equipped with a mechanical stirrer, reflux condenser, addition funnel, thermometer, and nitrogen inlet. The flask was charged with 19.58 g (0.408 mol) of 50% sodium hydride dispersion in mineral oil. The oil was washed off the sodium hydride with two 50 ml portions of toluene, then 175 ml of toluene added to the flask and the mixture warmed to 50° C. To the reaction mixture was added dropwise 81.69 g (0.408 mol) of diethyl cyclopropyl malonate. If the evoluation of hydrogen gas was not observed after a few grams of diethyl isopropylmalonate had been added, then a few drops of absolute ethanol was added to initiate the reaction. When all the diethyl isopropylmalonate had been added, the reaction mixture was warmed to 75° C. until the evoluation of hydrogen had ceased. The 1,1,3-trichloro-1-butene was added dropwise while maintaining the reaction temperature at 75° C. When all the halide had been added, the reaction mixture was refluxed overnight. The reaction mixture was then cooled to room temperature, and 25 ml of ice-water added dropwise. The reaction mixture was poured into 500 ml of ice-water and extracted into ether. The combined ether extracts were washed twice with water, dried (MgSO$_4$) and the ether removed. The residue was vacuum distilled through a vigreaux column to give 69.47 g (53% yield) of the desired malonate, b.p. 114°–120° C./0.3 mm.

NMR (CDCl$_3$,δ): 0.3–1.6 (m, 14H); 2.7–3.6 (m, 1H); 38–4.5 (q, 4H); 6.12 (d, 1H).

Part G: ethyl 5,5-dichloro-3-methyl-2-cyclopropyl-4-pentenoate.

A 1 liter flask fitted with a magnetic stirrer, reflux condenser, and nitrogen inlet was charged with 69.47 g (0.215 mol) of diethyl (3,3-dichloro-1-methyl-2-propenyl) cyclopropyl malonate, 7.74 g (0.430 mol) water, 44.25 g (0.430 mol) of sodium bromide, and 373 ml of dimethyl sulfoxide. This mixture was submerged in an oil bath heated to 180° C. for 5 hours during which a gas evolution occurred and ceased after 2½ hours. The reaction was cooled to room temperature and poured into 1 liter of water, extracted 4 times with 300 ml of ether, the combined ether extracts washed with water, dried (MgSO$_4$) and the ether removed. The residue was distilled through a vigreaux column to give 35.04 g (49% yield) of the desired ester as a colorless oil, b.p. 98°–100° C./0.6 mm.

NMR (CDCl$_3$,δ): 0.1–1.8 (m, 12H); 2.6–3.3 (m, 1H); 4.2 (q, 2H); 5.9 (t, 1H).

Part H: 5,5-dichloro-3-methyl-2-cyclopropyl-4-pentenoic acid

A 250 ml flask fitted with a magnetic stirrer, reflux condenser and nitrogen inlet was charged with 35.04 g (0.1395 mol) of ethyl 5,5-dichloro-3-methyl-2-cyclopropyl-4-pentenoate, 60 ml of ethanol, and 60 ml of water containing 16.76 g (0.4185 mol) of sodium hydroxide. The reaction mixture was refluxed for 18 hours, cooled, the ethanol removed under reduced pressure, and diluted with water. The aqueous layer was acidified with 6N HCl and extracted with ether, the ether extracts combined, washed with water, dried (MgSO$_4$) and the ether removed. The residue was vacuum distilled through a vigreaux column to give 18.92 g (60% yield) of the desired acid as a colorless oil, b.p. 120° C./0.3 mm.

NMR (CDCl$_3$,δ): 0.3–1.8 (m, 9H); 2.6–3.4 (m, 1H); 5.95 (pair of doublets, 1H); 11.45 (s, 1H).

EXAMPLE III 5,5-dichloro-3-methyl-2-cyclopropyl-4-pentenoic acid

Part A: diethyl (3,3-dichloro-1-methyl-2-propenyl) cyclopropyl malonate

A 1 liter flash was equipped with a mechanical stirrer, thermometer, additional funnel, and reflux condenser with nitrogen inlet. The flask was charged with 20.64 g (0.43 mol) of 50% sodium hydride dispersion in mineral oil and this was washed 2X with 50 ml of toluene followed by the addition of 200 ml of toluene. The suspension was warmed to 45° C., and 86.10 g (0.43 mol) of diethyl cyclopropyl malonate was added, dropwise, over a 2 hr. period. When all of the malonate had been added, the temperature was raised to 110° C. for 1 hr. then cooled to 60° C. The 1,1,3-trichloro-1-butene (68.56 g, 0.43 mol) was added dropwise at such a rate as to maintain the temperature at 60° C. When the addition was complete, the temperature was raised to 110° C. for 2 hr. The reaction mixture was cooled to room temperature and 10 ml of ice water added, dropwise, to destroy any remaining sodium hydride. This was followed by the addition of 200 ml of water, and the layers separated. The aqueous layer was extracted twice with 250 ml of ether, the extracts combined with the toluene, dried (MgSO$_4$), and the solvent removed. The residue was vacuum distilled through a vigreux column to give 63.73 g (46% yield) of the desired malonate.

NMR (CDCl$_3$, $\delta$): 0.53 (m,4H); 1.26 (t,6H); 1.20 (d,3H); 1.30 (m,1H); 3.23 (m, 1H); 4.20 (q,4H); 6.08 (d,1H).

Part B: ethyl 5,5-dichloro-3-methyl-2-cyclopropyl-4-pentenoate

A 1 liter flask was equipped with a magnetic stirrer and a reflux condenser with nitrogen inlet. The flask was charged with 107.56 g (0.333 mol) of diethyl (3,3-dichloro-2-propenyl) cyclopropyl malonate, 68.54 g (0.666 mol) of sodium bromide, 350 ml of dimethyl sulfoxide, and 12 ml (0.666 mol) of water. An oil bath was heated to 190° C. and the above reaction mixture lowered into the hot oil bath. The reaction mixture was stirred at 190° C. until no further gas evolution was observed (about 5 hr.). The reaction mixture was cooled to room temperature, diluted with water, and extracted thoroughly with ether. The ether was washed with water, dried (MgSO$_4$), and stripped. The residue was vacuum distilled to give 67.10 g (80% yield) of the desired produce, b.p. 67°-84° C./0.15 mm.

NMR (CDCl 3,$\delta$): 0.5–0.85 (m,4H); 1.10 (pair of doublets, 3H); 1.35 (t,3H); 0.90–2.2 (m,2H); 3.05 (m,1H); 4.20 (q,2H); 5.90 (pair of doublets, 1H).

Part C: 5,5-dichloro-3-methyl-2-cyclopropyl-4-pentenoic acid

A 500 ml flask was equipped with a magnetic stirrer and a reflux condenser with a nitrogen inlet. The flask was charged with 57.0 g (0.227 mol) of ethyl 5,5-dichloro-3-methyl-2-cyclopropyl-4-pentenoate, 27.24 g (0.681 mol) of sodium hydroxide, 97 ml of water, and 97 ml of ethanol. The reaction mixture was refluxed for four days. After cooling to room temperature, most of the ethanol was removed on the rotary evaporator, the residue diluted with water and extracted twice with ether. The aqueous layer was acidified with concentrated hydrochloric acid, and extracted three times with ether. The combined ether extracts were washed twice with water, dried (MgSO$_4$), and the solvent removed to leave 45.82 g (90% yield) of a honey colored oil.

IR (neat, cm$^{-1}$): 3500–2400 (broad, S), 3080(s), 2970(s), 2930(s), 1700(s), 1620(m), 1465(w), 1460(w), 1420(m), 1380(w), 1290(s), 1220(s), 1180(w), 1140(w), 1050(w), 1025(m), 985(w), 935(w), 905(s), 860(s), 825(m), 795(w), 765(w).

NMR (CDCl$_3$): 0.10–0.90 (m,4H); 1.18 (pair of doublets, 3H); 0.90–3.50 (m,3H); 5.93 (pair of doublets, 1H); 11.65 (s, broad, 1H).

EXAMPLE IV 5,5-dichloro-3-methyl-2-isopropyl-4-pentenoic acid

Part A: 1-trimethylsilyloxy-1-ethoxy-3-methyl-1-butene

A 1 liter flask was equipped with a mechanical stirrer, a reflux condenser, an additional funnel, nitrogen inlet, and thermometer. The glassware was dried carefully and charged with 225 ml of tetrahydrofuran, 30.36 g (0.300 mol) of diisopropylamine, and cooled to 0° C. Over a 30 minute period, 190 ml (0.300 mol) of 1.6M n-butyl lithium in hexane was added. The reaction mixture was stirred at 0° C. for 15 minutes, then cooled to −76° C. and 39.06 g (0.300 mol) of ethyl isovalerate added dropwise over ~15 min. When addition was complete, the reaction mixture was stirred for 15 min. at −76° C., then 82 ml (0.88 mol) of chlorotrimethylsilane added dropwise. When addition was complete, the Dry Ice-acetone bath was removed and the reaction mixture stirred for 1½ hours while coming up to room temperature.

The reaction mixture was filtered and concentrated under reduced pressure. The residue was taken up in ether and filtered. The filtrate was concentrated on the rotary evaporator, then vacuum distilled through a vigreux column to give 52.29 g (86% yield) of the desired ketene acetal, b.p. 79°–86° C./31 mm.

NMR (CDCl$_3$,$\delta$): 0.22 (s,9H); 0.95 (d,6H); 1.21 (t,3H); 2.50 (m,1H); 3.76 (m,2H).

Part B: 1,1,3-trichloro-1-butene

A 3 liter flask was equipped with a mechanical stirrer, an addition funnel, and a reflux condenser with N$_2$ inlet. The flash was charged with 1500 ml of pentane, 159.25 g (2.45 mol) of powdered potassium hydroxide, and approximately 1.0 g of dicyclohexyl-18-crown-6 ether. The reaction mixture was heated to reflux and 393.16 g (1.64 mol) of 1,1,1-trichloro-3-bromobutane added dropwise. The reaction mixture was refluxed 24 hr., during which time the white suspension of potassium hydroxide disappeared and was replaced by a dark precipitate. The reaction mixture was cooled to room temperature, washed three times with water, dried (MgSO$_4$), and fractionally distilled through a vigreux column. The material with b.p. 79°–93° C./100 mm proved to be the desired 1,1,1-trichloro-2-butene, 217.17 g (83% yield).

NMR(CDCl$_3$,$\delta$): 1.85 (d,3H); 6.20 (m,2H).

146.07 g (0.92 mol) of 1,1,1-trichloro-2-butene was stirred at room temperature under nitrogen with 5.8 g of anhydrous zinc chloride. During this time the temperature of the reaction mixture was prevented from exceeding 50° C. by intermittent use of an ice bath. The light yellow liquid was decanted from the zinc chloride to give 134.51 g (92% yield).

NMR (CDCl$_3$): 1.65 (d,3H); 4.87 (m,1H); 6.05 (d,1H).

Part C: ethyl 5,5-dichloro-3-methyl-2-isopropyl-4-pentenoate

A 250 ml R.B. flask was equipped with a magnetic stirrer, reflux condenser, and N$_2$ inlet tube. The glassware was dried thoroughly then charged with 23.91 g (0.15 mol) of 1,1,3-trichloro-1-butene, 30.36 g (0.15 mol) of 1-trimethylsilyloxy-1-ethoxy-3-methyl-1-butene, 100 ml of methylene chloride, and ~0.50 g of anhydrous zinc chloride. The reaction mixture was stirred at room temperature and monitored by infrared. The gradual disappearance of the ketene acetal C=C peak at 1675 cm$^{-1}$ and the appearance of an ester C=O peak at 1720 cm$^{-1}$ was observed. The reaction mixture after 67 hours showed only a C=O peak at 1720 cm$^{-1}$ and no 1675 cm$^{-1}$ and was diluted with 150 ml of methylene chloride, washed with 5X 100 ml of 5% sodium bicarbonate solution, the 2X with 50 ml of water. The methylene chloride was dried (MgSO$_4$), stripped, and the residue vacuum distilled through a vigreux column to give 23.41 g (62% yield) of the desired product, b.p. 64°–68° C./0.30 mm.

Part D: 5,5-dichloro-3-methyl-2-isopropyl-4-pentenoic acid

A solution of 23.41 g (0.0925 mol) of ethyl 5,5-dichloro-3-methyl-2-isopropyl-4-pentenoate, 11.10 g (0.278 mol) of sodium hydroxide, 40 ml of water, and 40 ml of ethanol was refluxed for 3 days under N$_2$. The solvent was concentrated on the rotary evaporator, the residue taken up in 300 ml of water and extracted 2X with ether. The aqueous layer was acidified with conc. HCl, then extracted 3X with 150 ml of ether. The combined ether extracts were washed with water, dried (MgSO$_4$), and stripped to give 17.09 g (82% yield) of the desired acid.

NMR (CDCl$_3$,δ): 1.08(m 9H); 2.10(m,2HO); 2.90(m,1H); 5.70 and 6.20 (d,pair,1H); 10.75(s,1H).

EXAMPLE V 5,5-dichloro-3-methyl-2-isopropyl-4-pentenoic acid

Part A: 1,1,1-trichloro-3-bromobutane

A 3 l Adkins stainless steel bomb was thoroughly cleaned, dried and purged with nitrogen. The bomb was charged with 594.8 g (3.0 mol) of bromotrichloromethane 5.00 g (0.02 mol) dibenzoyl peroxide. The bomb was then sealed and cooled in a dry-ice acetone bath for 30 minutes. The bomb was then charged with 69 g (1.62 mol) propylene via a small hoke cylinder. The bomb was then agitated and heated for 4 hours during which time a temperature rise of 44° C. and a pressure increase of 100 PSIG was observed within 15 minutes. The reaction mixture was an almost colorless liquid which was vacuum distilled through a vigreaux column to give 286.2 g (73% yield) of the desired product b.p. 59°–65° C./10 mm.

NMR (CDCl$_3$,δ): 1.85 (d, 3H); 3.32 (m, 2H); 4.40 (m, 1H).

Part B: 1,1,1-trichloro-2-butene

A 1 l flask was equipped with a magnetic stirrer, additional funnel, and nitrogen inlet. The flask was charged with 30.6 g (0.464 mol) of 85% potassium hydroxide dissolved in 100 ml of ethanol and the solution cooled in a salt-ice bath. To this solution was added dropwise 120.22 g (0.5 mol) of 1,1,1-trichloro-3-bromobutane in 100 ml of ethanol over a 1 hour period. A white precipitate forms upon the addition of the butane. After the addition was complete the reaction mixture was stirred for 3½ hours at 0° C. The reaction mixture was diluted with 1800 ml of cold water and extracted three times with 300 ml portions of hexane. The combined hexane extracts were washed with water, dried (MgSO$_4$) and concentrated by distillation at atmospheric pressure. The residue was vacuum distilled through a vigreaux column to give 43.08 (55% yield) of 1,1,1-trichloro-2-butene, b.p. 72°–79° C./100 mm.

NMR (CDCl$_3$, δ): 1.87 (d, 3H); 6.25 (m, 2H).

Part C: diethyl isopropyl (3,3-dichloro-1-methyl-2-propenyl) malonate

A 1 l flask was equipped with a mechanical stirrer, reflux condenser, addition funnel, thermometer, and nitrogen inlet. The flask was charged with 11.04 (0.23 mol) of 50% sodium hydride dispersion in mineral oil. The oil was washed off the sodium hydride with two 50 ml portions of toluene, then 175 ml of toluene added to the flask and the mixture warmed to 50° C. To the reaction mixture was added dropwise 46.5 g (0.23 mol) of diethyl isopropylmalonate. If the evolution of hydrogen gas was not observed after a few grams of diethyl isopropylmalonate had been added, then a few drops of absolute ethanol was added to initiate the reaction. When all the diethyl isopropylmalonate had been added, the reaction mixture was warmed to 75° C. until the evolution of hydrogen had ceased. To the reaction mixture 37 g (0.23 mol) 1,1,1-trichloro-2-butene was added dropwise while maintaining the reaction temperature at 75° C. When all the halide had been added, the reaction mixture was refluxed overnight. The reaction mixture was then cooled to room temperature, and 25 ml of ice-water added dropwise. The reaction mixture was added dropwise. The reaction mixture was poured into 500 ml of ice water and extracted into ether. The combined ether extracts were washed twice with water, dried (MgSO$_4$), and the ether removed. The residue was vacuum distilled through a vigreaux column to give 17.02 g (23% yield) of diethyl isopropyl (3,3-dichloro-1-methyl-2-propenyl) malonate, b.p. 105°–107° C./0.3 mm.

NMR (CDCl$_3$,δ): 1.18 (m, 15H); 2.3 (m, 1H); 3.42 (m, 1H); 4.27 (q 4H); 6.08 (d, 1H).

Part D: ethyl 5,5-dichloro-3-methyl-2-isopropyl-4-pentenoate

A 1 l flask was equipped with a magnetic stirrer, reflux condenser and nitrogen inlet. The flask was charged with 46 g (0.14 mol) of diethyl isopropyl (3,3-dichloro-1-methyl-2-propenyl) malonate prepared as per method C, 14.4 g (0.14 mol) of sodium bromide, 5.04 g (0.28 mol) water, and 103 ml of dimethyl sulfoxide. The reaction flask was submerged to the neck in an oil bath preheated to 190° C. for 5 hours, then overnight and the reaction temperature achieves 155° C. with a vigorous reflux. The reaction mixture was cooled and added to 500 ml cold water. The mixture was extracted three times with 300 ml of ethyl ether, the combined ether extracts washed with water, dried (MgSO$_4$) and the ether removed. The residual oil was distilled through a vigreaux column to glue 10.25 g (30% yield) of ethyl 5,5-dichloro-3-methyl-2-isopropyl-4-pentenoate, b.p. 65° C./0.1 mm.

NMR (CDCl$_3$, δ): 1.16 (m, 12H); 2.1 (m, 2H); 3.0 (m, 1H); 4.21 (q, 2H); 5.70, 6.21 (pair of doublets, 1H).

Part E: 5,5-dichloro-3-methyl-2-isopropyl-4pentenoic acid

A 250 ml flask fitted with reflux condenser and nitrogen inlet was charged with 10 g (0.039 mol) of ethyl 5,5-dichloro-3-methyl-2-isopropyl-4-pentenoate, 5.46 g (0.079 mol) of potassium carbonate, 133 ml methanol, and 44.5 ml water. The reaction mixture was refluxed for 2 days, cooled, and the methanol removed under reduced pressure and extracted with ether. The aqueous layer was then acidified with conc. HCl, extracted with ether, washed once with water, dried (MgSO$_4$), and the ether removed to 0.84 g (18% yield) of a tan oil. The neutral ether layer was dried (MgSO$_4$) and the ether removed to leave 8.19 g of starting pentenoate.

IR (neat, cm$^{-1}$) 3500–2500 (s); 1700 (s); 1620 (m); 1460 (m); 1420(m); 1390(m); 1370 (w); 1280 (m); 1260 (m); 1235 (m); 1220 (m); 1180 (w); 1160 (w); 910 (m); 900 (m); 890 (m); 860 (m) 820 (w).

NMR (CDCl$_3$, δ): 0.07–1.50 (m, 9H); 2.15 (m, 2H); 2.93 (m, 1H); 5.8–6.25 (pair of doublets, 1H), 12.10 (s, 1H).

The following procedure is preferred:

A 100 ml flask fitted with a reflux condenser and nitrogen inlet was charged with 8.19 g (0.032 mol) of ethyl 5,5-dichloro-3-methyl-2-isoproply-4-pentenoate, 13.6 ml of ethanol and 13.6 ml of water containing 3.84 g (0.096 mol) of sodium hydroxide. The reaction mixture was heated to reflux for 64 hours. The ethanol was removed under reduced pressure and the residue diluted with 150 ml of water. The mixture was extracted with ethyl ether and the acidified with conc. HCl. The acidified aqueous layer extracted 3 times with 250 ml of ethyl ether, the combined ether extracts washed with water, dried (MgSO$_4$) and the ether removed to yield 6.11 g (82% yield) of a tan oil.

IR Same as above (Part E this Example)
NMR Same as above (Part E this Example)

Additional halo-4-alkenoic acids which have been prepared to date and their physical properties are summarized in Table II.

The novel halo-4-alkenoic acids disclosed in this memorandum are illustrated by, but not limited to, the following:

5,5-dichloro-2-isopropyl-3-methyl-4-pentenoic acid
5,5-dichloro-2-isopropyl-3-ethyl-4-pentenoic acid
5,5-dichloro-2,3-diisopropyl-4-pentenoic acid
5,5-dichloro-2-isopropyl-3-trifluoromethyl-4-pentenoic acid
5,5-dichloro-2-isopropyl-3,3-dimethyl-4-pentenoic acid
5,5-dichloro-2-isopropyl-3-vinyl-4-pentenoic acid
5,5-dichloro-2-isopropyl-3-cyclopropyl-4-pentenoic acid
5,5-dichloro-2-isopropyl-3-cyclobutyl-4-pentenoic acid
5,5-dichloro-2-isopropyl-3-cyano-4-pentenoic acid
5,5-dichloro-2-isopropyl-3-nitro-4-pentenoic acid
5,5-dichloro-2-isopropyl-3-methoxy-4-pentenoic acid
5,5-dichloro-2-isopropyl-3-phenoxy-4-pentenoic acid
5,5-dichloro-2-isopropyl-3-methylsulfenyl-4-pentenoic acid
5,5-dichloro-2-isopropyl-3-phenylsulfenyl-4-pentenoic acid
5,5-dichloro-2-isopropyl-3-methylsulfinyl-4-pentenoic acid
5,5-dichloro-2-isopropyl-3-methylsulfonyl-4-pentenoic acid
5,5-dichloro-2-isopropyl-3-phenylsulfonyl-4-pentenoic acid
5,5-dichloro-2-isopropyl-3-acylamido-4-pentenoic acid
5,5-dichloro-2-isopropyl-3-dimethylamino-4-pentenoic acid
5,5-dibromo-2-cyclobutyl-4-pentenoic acid
5,5-dibromo-2-isopropyl-3-methyl-4-pentenoic acid
5,5-dibromo-2-isopropyl-3-ethyl-4-pentenoic acid
5-chloro-3-methyl-2-isopropyl-4-hexenoic acid
5-chloro-3-trifluoromethyl-2-isopropyl-4-hexenoic acid
5-chloro-2-cyclopropyl-4-hexenoic acid
5-chloro-2-tert-butyl-4-hexenoic acid
5-chloro-2-sec-butyl-4-hexenoic acid
5-chloro-2-isopropyl-4-pentenoic acid
5-chloro-3-methyl-2-isopropyl-4-pentenoic acid
5-chloro-2-cyclopropyl-4-pentenoic acid
5-chloro-2-tert-butyl-4-pentenoic acid
5-chloro-2-(1-methylbutyl)-4-pentenoic acid
5-bromo-2-isopropyl-3-methyl-4-pentenoic acid
5-bromo-2-cyclopropyl-4-pentenoic acid
5-bromo-2-tert-butyl-4-pentenoic acid
5-bromo-2-isoamyl-4-pentenoic acid
5-bromo-4-methyl-2-isopropyl-4-pentenoic acid
4,5-dibromo-2-isopropyl-4-pentenoic acid
4,5,5-trichloro-2-isopropyl-4-pentenoic acid
4,5,5-tribromo-2-isopropyl-4-pentenoic acid
5,5-dichloro-4-methyl-2-isopropyl-4-pentenoic acid
4-chloro-2-cyclopropyl-4-hexenoic acid
4-chloro-5-methyl-2-isopropyl-4-hexenoic acid
4,5-dichloro-2-isopropyl-4-pentenoic acid
4,5-dichloro-2-cyclopropyl-4-pentenoic acid
4,5-dichloro-2-tert-butyl-4-pentenoic acid
4,5-dichloro-2-isoamyl-4-pentenoic acid
5,5-dichloro-2-cyclopropyl-4-pentenoic acid
5,5-dichloro-2-cyclopropyl-3-methyl-4-pentenoic acid
5,5-dichloro-2-cyclopropyl-3,3-dimethyl-4-pentenoic acid
5,5-dichloro-2-cyclobutyl-4-pentenoic acid
5,5-dichloro-2-cyclobutenyl-4-pentenoic acid The pysical properties of halo-4-alkenoic acids prepared as described in the examples hereinabove are tabulated in Table II hereinbelow.

EXAMPLES VI–XVIII

Following procedures similar to those described in examples I–V, further compounds according to the invention were prepared. The physical characteristics are given in Table II in which the compounds are identified by reference to their structure formula:

TABLE II

| Example | Structure | IR (meat, cm$^{-1}$) | NMR (CDCl$_3$, δ) |
|---|---|---|---|
| VI | Cl\\C=C/H / Cl / \\CH$_2$CHCO$_2$H (cyclopentyl) | 3500–2500 (s), 2955 (s), 2940 (s), 2870 (s), 1700 (s), 1620 (m), 1446 (m), 1330 (w), 1290 (m), 1245 (m), 1220 (m), 1090 (w), 940 (w), 890 (m), 820 (w). | 0.15–3.15 (m, 12H); 5.95 (m, 1H); 11.95 (s, 1H). |
| VII | Cl\\C=C/H / Cl / \\CH—CHCO$_2$H / CH$_3$ (isopropyl) | 3500–(s), 1700 (u), 1620 (m), 1466 (m), 1420 (m), 1340 (w), 1376 (w), 1310 (m), 1280 (m), 1260 (m), 1235 (m), 1220 (m), 1180 (w), 1160 (w), 910 (m), 900 (m), 890 (m), 860 (m), 820 (w). | 0.70–1.50 (m, 9H); 215 (m, 2H); 2.93 (m, 1H); 5.8–6.25 (pair of doublets, 1H), 12.10 8s, 1H). |

TABLE II-continued

Physical Properties of Halo-4-Alkenoic Acids

| Example | Structure | IR (meat, cm$^{-1}$) | NMR (CDCl$_3$, δ) |
|---|---|---|---|
| VIII | Cl\C=C/H, Cl/ \CH$_2$CHCO$_2$H (cyclopropyl) | 3500–2500 (s), 3038 (s), 3005 (s), 2920 (s), 1705 (s), 1620 (m), 1420 (m), 1240 (m), 1250 (w), 1230 (m), 1140 (w), 10050 (w), 1020 (m), 940 (m), 920 (m), 890 (m), 840 (w), 820 (m). | 0.1–1.3 (m, 5H); 1.70 (m, 1H); 2.55 (t, 2H); 6.00 (t, 1H); 11.90 (s, 1H). |
| IX | H\C=C/H, Cl/ \CH$_2$CHCO$_2$H (isopropyl) | 3500 2500 (u), 2960 (s), 2930 (s), 2870 (s), 1700 (s), 1630 (m), 1460 (m), 1440 8m), 1420 (m), 1340 (w), 1370 (w), 1340 8w), 1280 8m), 1260 (m), 1220 (m), 1180 8w), 935 (m), 840 8w), 750 (w), 710(w). | 0.90 (t, 6H); 2.25 (m, 4H); 5.95 (m, 2H); 11.9 (s, 1H). |
| X | Cl\C=C/Cl, Cl/ \CH$_2$CHCO$_2$H (isopropyl) | 3500–2500 (s), 2960 (s), 2430 (s), 2870 (s), 1705 (u), 1800 (m), 1460 (m), 1430 (m), 1390 (w), 1370 (w), 1290 (m), 1240 (m), 1220 (m), 1200 (w), 920 (s), 770 (w). | 1.05 (d, 6H); 1.95 (m, 1H); 2.80 (m, 3H); 11.4 8s, 1H). |
| XA | Cl\C=C/Cl, H/ \CH$_2$CHCO$_2$H (isopropyl) | 3500–2500 (u), 2960 (s), 2930 (s), 2870 (u), 1705 8s), 1608 (w), 1460 (m), 1430 (m), 1390 (w), 1370 (w), 1290 (m), 1240 (m) 1220 (m), 1200 (w), 1040 (w), 930 (m), 810 (m), 730 (w). | 1.03 (d, 6H); 2.03 (m, 1H); 2.78 (m, 3H); 6.20 (s, 1H); 12.03 (s, 1H). |
| XI | Cl\C=C/H, Cl/ \CH—CHCO$_2$H, CH$_3$ (cyclopropyl) | 3500–2500 (m), 3080 (s) 3000 (s), 2970 (s), 2930 (s), 2880 (s), 1700 (s), 1620 (m), 1460 (w), 1420 (m), 1290 (m), 1220 (m), 1056 (w), 1620 (m), 900 (m), 860 (m), 820 (w). | 0.1–1.1 (m, 5H); 1.20 (pair of doublets 3H); 1.60 (m, 1H); 3.05 (m, 1H); 5.75 (pair of doublets); 11.47 (s, 1H). |
| XII | Cl\C=C/H, Cl/ \CH—CHCO$_2$H, CH$_2$CH$_3$ (isopropyl) | 3500–2500 (m), 2460 (s), 2870 (s), 1700 (s), 1620 (m), 1460 (m), 1420 (m), 1390 (w), 1370 (w), 1280 (m), 1240 (m), 1220 (s), 1180 (m), 1130 (w), 915 (m), 880 (m), 865 (m), 845 (m), 820 (w), 775 (w), 740 (w). | 1.0 (d, 6H); 1.0–2.5 (m, 7H); 2.78 (m, 1H); 5.6 and 6.18 (pair of doublets, 1H); 10.2 (S erased, 1H). |
| XIII | Cl\C=C/H, CH$_3$, Cl/ C—CHCO$_2$H, CH$_3$ (isopropyl) | 3500–2500 (m), 2950 (s), 2870 (s), 1700, 1610 (w), 1450 (m), 1410 (m9, 1390 (m), 1365 (m), 1250 (m), 1160 (w), 1100 (w), 1010 (w), 870 (m) | 1.03 (pair of doublets, 6H); 1.33 (s, 6H9; 2.1 (m, 1H); 2.58 (d, 1H); 6.1 (s, 1H); 11.4 (s, erased, 1H). |
| XIV | Cl\C=C/H, CH$_3$, Cl/ CH—CHCO$_2$H, CH$_3$ (isopropyl) | 3500–2500 (m), 2990 (s), 2950(s), 1705 (s), 1620 (m), 1460 (m) 1420 (m), 1380 (w), 1240 (m), 1240 (m), 980 (w), 940 (w), 900 (s), 870 (m). | 1.18 (pair of doublets, 6H); 2.1–3.3 (m, 2H); 5.90 (pair if doublets), 11.85 (s, erased, 1H) |

TABLE II-continued
Physical Properties of Halo-4-Alkenoic Acids

| Example | Structure | IR (meat, cm$^{-1}$) | NMR (CDCl$_3$, δ) |
|---|---|---|---|
| XV | Cl$_2$C=C(H)–CH(CH$_3$)–CH(CH$_2$CH$_3$)CO$_2$H | 2500–2500 (m), 2980 8s), 2950 (s), 2895 (s), 1705 (s), 1620 (m), 1460 (m), 1420 (m), 1395 (w), 1285 (m), 1220 (m), 960 (m), 920 (s), 885 (s), 860 (s), 790 (w) | 1.0 (m, 6H); 1.5 (q, 2H); 2.0–3.1 (m, 2H); 5.81 (pair of doublets); 9.45 (s, erased, 1H) |
| XVI | Cl$_2$C=C(H)–C(CH$_3$)$_2$–CH(CH$_2$CH$_3$)CO$_2$H | 3500–2500 (m), 2490 (s), 2450 (s), 2890 (s), 1700 (s) 1610 (m), 1465 (m), 1420 (m), 1395 (m), 1375 (m), 1275 (s), 1230 (s), 1180 (s), 1100 (m), 1025 (m), 950 (m), 880 (s), 810 (w), 740 (w), 620 (w). | 0.90 (t, 3H); 1.30 (s, 6H); 1.10–2.60 (m, 3H); 6.05 (s, 1H); 11.75 (s, 1H). |
| XVII | Cl$_2$C=C(H)–CH(CH$_3$)–CH(cyclopentyl)CO$_2$H | 3500–2500 (m), 3650 (m), 2460 (s), 2840 (s), 1700 (s9, 1620 (m), 1455 (m), 1420 (m), 1380 (w), 1260 (m), 1220 (s), 1150 (w), 940 (m9, 915 8s), 890 (s), 870 (s), 785 (w), 700 (w). | .130 (d, 3H); 1.30–2.60 (m, 10 H); 2.90 (m, 1H); 6.05 (pair ddoublets, 1H9; 10.58 (s, erased, 1H). |
| XVIII | Cl$_2$C=C(H)–C(CH$_3$)$_2$–CH(cyclopropyl)CO$_2$H | 3500–2500 (m), 3100 (m), 3030 (s), 2995 (s), 2950 (s), 2900 (s), 1705 (s), 1620 (m), 1470 (m), 1426 (m), 1400 (w), 1375 (s), 1290 (m), 1246 (m), 1030 (s), 880 (s), 835 (w). | 0.10–1.30 (m, 6H); 1.35 (s, 5H); 1.71 (d, 1H); 6.13 (s, 1H); 8.73 (s, erased, 1H) |

Using procedures similar to those described in examples I–V further acid compounds according to this invention were prepared for comparison with acid compounds disclosed in Belgium Pat. No. 862,499. Table III compares the insecticidal activity (LD$_{50}$ ppm) of pyrethroids prepared from these acids to prior art esters in which R$_4$ and R$_5$ are hydrogen. It clearly can be seen that a single methyl group at C$_3$ substantially enhances the broad spectrum insecticidal activity over those esters having only hydrogen at C$_3$ or those having two methyl groups at C$_3$. Thus, compare example 19 with 20, 21 with 22 and 25 with 26.

The pesticidal activity of the compounds listed in Table III were determined against mites and certain insects including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted the test insects. For testing purposes, the number of aphids per pot was standarized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Prodenia eridania*, (Cram,)), reared on Tendergreen bean plants at a temperature of 80±5 ° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls), reared on Tendergreen bean plants at a temperature of 80±5° F. and 50±5 percent relative humidity were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.) reared according to the specifications of the Chemical Specialties Manufacturing Association (Blue Book, McNair-Dorland Co., N.Y. 1954; pages 243–244, 261) under controlled conditions of 80±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80±5° F. and the relative humidity of 50±5° percent. Flies which showed no sign of movement on prodding were considered dead.

Mite Foliage Spray Test

Adults and numphal stages of the two-spotted mite (*Tetranychus urticae* Koch), reared on Tendergreen bean plants at 80±5° percent relative humidity, were the test organisms. Infested leaves from a stock culture were placed on the primary leaves of two beam plants six to eight inches in height, growing in a two-and-a-half inch clay pot. 150–200 mites, a sufficient number of testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig, air pressure. This application, which lasted 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

The results of these tests are set forth in Table III below;

TABLE III

| Example | Structure | Aphid | Mite | Southern armyworm | *MBB | **HF |
|---|---|---|---|---|---|---|
| 19*** | (Cl)₂C=C(H)-CH₂CH(iPr)CO₂CH(CN)-3-phenoxyphenyl | 5 | 330 | 70 | 24 | 50 |
| 20 | (Cl)₂C=C(H)-CH(CH₃)-CH(iPr)CO₂CH(CN)-3-phenoxyphenyl | 0.5 | 200 | 104 | 3 | 38 |
| 21**** | (Cl)₂C=C(H)-CH₂CH(Et)CO₂CH(CN)-3-phenoxyphenyl | 16 | >500 | >500 | >500 | >500 |
| 22 | (Cl)₂C=C(H)-CH(CH₃)-CH(Et)CO₂CH(CN)-3-phenoxyphenyl | 4 | ~120 | 49 | 9 | 66 |
| 23 | (Cl)₂C=C(H)-C(CH₃)₂-CH(iPr)CO₂CH(CN)-3-phenoxyphenyl | >400 | i | >500 | ~500 | i |
| 24 | (Cl)₂C=C(H)-C(CH₃)₂-CH(Et)CO₂CH(CN)-3-phenoxyphenyl | ~500 | >500 | >500 | >100 | >500 |
| 25 | (Cl)₂C=C(H)-CH₂-CH(cyclopropyl)CO₂CH(CN)-3-phenoxyphenyl | 11 | >500 | >500 | >500 | >500 |

TABLE III-continued

| Example | Structure | Aphid | Mite | Southern armyworm | *MBB | **HF |
|---|---|---|---|---|---|---|
| 26 | 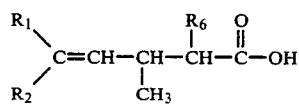 | 0.4 | 250 | 25 | 3 | 39 |

*Mexican Bean Beetle
**Housefly
*** &
****Prior art compounds disclosed in Belgium Patent 860, 867

What is claimed is:

1. A halo-4-alkenoic acid compound of the structure:

$$\begin{array}{c} R_1 \\ \phantom{R}\diagdown \\ \phantom{RRR}C=CH-CH-CH-C-OH \\ \phantom{R}\diagup \phantom{RRRRR} | \phantom{RR} | \phantom{R} \| \\ R_2 \phantom{RRRRR} CH_3 \phantom{RR} R_6 \phantom{R} O \end{array}$$

wherein:
$R_1$ and $R_2$ independently halogen; and
$R_6$ is $C_1$ is $C_3$ alkyl or cycloalkyl.

2. A compound as defined in claim 10 wherein $R_1$ and $R_2$ are chloro.
3. 5,5-dichloro-2-cyclopropyl-3-methyl-4-pentanoic acid.
4. 5,5-dichloro-2-ethyl-3-methyl-4-pentanoic acid.
5. 5,5-dichloro-2-isopropyl-3-methyl-4-pentenoic acid.